(12) United States Patent
Kawahara et al.

(10) Patent No.: US 7,896,876 B2
(45) Date of Patent: Mar. 1, 2011

(54) HIGH FREQUENCY INCISION INSTRUMENT FOR ENDOSCOPE

(75) Inventors: Yoshiro Kawahara, Okayama (JP); Hiroaki Shibata, Saitama (JP)

(73) Assignee: Hoya Corporation, Tokyo (JP)

( * ) Notice: Subject to any disclaimer, the term of this patent is extended or adjusted under 35 U.S.C. 154(b) by 1157 days.

(21) Appl. No.: 11/589,040

(22) Filed: Oct. 30, 2006

(65) Prior Publication Data
US 2007/0100337 A1 May 3, 2007

(30) Foreign Application Priority Data
Oct. 31, 2005 (JP) .................. P2005-315863

(51) Int. Cl.
*A61B 18/18* (2006.01)
*A61B 18/14* (2006.01)

(52) U.S. Cl. .............. 606/46; 606/45; 600/121; 600/152; 600/156

(58) Field of Classification Search ............. 606/32–50; 600/562–565; 285/281, 345, 347
See application file for complete search history.

(56) References Cited

U.S. PATENT DOCUMENTS

| 5,919,188 A * | 7/1999 | Shearon et al. ............ 606/41 |
| 2005/0261675 A1* | 11/2005 | Shibata ................... 606/45 |
| 2006/0173450 A1 | 8/2006 | Shibata |
| 2006/0173451 A1 | 8/2006 | Shibata |

FOREIGN PATENT DOCUMENTS

| JP | 61-7694 | 3/1986 |
| JP | 2001-245897 | 9/2001 |
| JP | 2004-152632 * | 5/2004 |
| JP | 2005-334000 | 12/2005 |
| JP | 2006-212109 | 8/2006 |
| JP | 2006-212110 | 8/2006 |

OTHER PUBLICATIONS

English Language Abstract of JP 2005-334000.
English Language Abstract of JP 2001-245897.

* cited by examiner

*Primary Examiner* — Michael Peffley
*Assistant Examiner* — Ronald Hupczey, Jr.
(74) *Attorney, Agent, or Firm* — Greenblum & Bernstein P.L.C.

(57) ABSTRACT

A high-frequency incision instrument for an endoscope is provided with an electrically insulative flexible sheath constituted of a distal tube disposed at a tip portion thereof and a proximal tube disposed on a proximal side such that one is loosely inserted into the other so as to rotate around an axial line thereof, a high-frequency electrode exposed along a lateral surface of the distal tube and connected to a conductive operating wire extending throughout inside the distal tube and the proximal tube, so that a high-frequency current is supplied to the high-frequency electrode through the operating wire, and so that rotating the operating wire at a proximal end portion of the proximal tube around an axial line causes the distal tube to rotate around the axial line with respect to the proximal tube, thus to change an orientation of the high-frequency electrode.

4 Claims, 12 Drawing Sheets

HIGH FREQUENCY INCISION INSTRUMENT FOR ENDOSCOPE

CROSS-REFERENCE TO RELATED APPLICATIONS

The present application claims priority under 35 U.S.C. §119 of Japanese Patent Application No. 2005-315863, filed on Oct. 31, 2005, which is expressly incorporated herein by reference in its entirety.

BACKGROUND OF THE INVENTION

The present invention relates to a high-frequency incision instrument for an endoscope, to be inserted through an instrument insertion channel of the endoscope for executing an endoscopic mucosal resection (EMR) and other procedures.

Operational procedures adopted in the endoscopic mucosal resection include injecting physiological saline solution under a mucous membrane to be resected to thereby bulge the portion thereof to be resected, and incising the base portion of the bulge in a horizontal direction, with the high-frequency incision instrument.

For such purpose, a high-frequency incision instrument for an endoscope with a high-frequency electrode exposed along a side of a distal portion of an insulative flexible sheath, such as the one disclosed in Japanese Utility Model Publication No. SHO 61-7694, has been suitably employed.

FIG. 9 illustrates a process of the endoscopic mucosal resection with a high-frequency incision instrument for an endoscope. A tip portion of a flexible sheath 1 projecting into a body cavity through an instrument insertion channel of the endoscope (not shown) is horizontally moved by manipulation of the endoscope, so as to resect a base portion of a bulge 100 of a mucous membrane with a wire-shaped high-frequency electrode 2, through which a high-frequency current is supplied.

The high-frequency electrode 2 is disposed along an outer surface of the flexible sheath 1 between a pair of through holes 4A, 4B perforated on a lateral surface close to the tip portion of the flexible sheath 1, and connected to a conductive operating wire (not shown) inserted through the flexible sheath 1.

When thus performing the endoscopic mucosal resection, in the case where the bulge 100 to be resected is larger than the high-frequency electrode 2 as shown in FIG. 9, it is impossible to completely resect the bulge 100 by a single resecting action, and hence the resecting action has to be repeated several times.

However, the flexible sheath 1 is interfered with by the bulge 100 on its way back to the initial position, after partially resecting the bulge 100, for performing the next resection. Accordingly, the endoscope has to be operated to move the flexible sheath 1 so as to avoid the interference with the bulge 100, which incurs considerable trouble in accurately setting the flexible sheath 1 on the initial position for the next incision.

To minimize such trouble, inverting the orientation of the high-frequency electrode 2, as shown in FIG. 10, by rotating only the tip portion of the flexible sheath 1 to which the high-frequency electrode 2 is attached, around an axial line thereof through a manipulation by hand, enables quickly setting the flexible sheath 1 on the initial position for the next incision. This invention has already been applied for a patent, under Japanese Patent Application No. 2004-152632, which has now been published as Japanese Patent Provisional Publication No. 2005-334000.

The flexible sheath 1 of such high-frequency incision instrument for an endoscope basically includes a short distal tube 1A to which the high-frequency electrode 2 is attached, loosely inserted so as to rotate around the axial line, into a tip portion of a long proximal tube 1B, larger (or smaller) in diameter than the distal tube 1A and extending to reach the operator.

Meanwhile, upon supplying the high-frequency current to the high-frequency electrode 2 thus to perform the mucosal resection, during the use of the high-frequency incision instrument for an endoscope, burnt residuum may splash around thereby disturbing the endoscopic observation for confirming the position to be resected next. In such case, as indicated by arrows W in FIG. 11, irrigation water has to be injected from the through holes 4A, 4B (or an independently provided water injection outlet), to wash away the burnt residuum.

From such viewpoint, the foregoing flexible sheath 1 insert-connected to the mating tube of a different diameter is not capable of injecting the irrigation water, because, as indicated by arrows W in FIG. 12, the irrigation water leaks out forward through the joint portion between the sheath and the tube.

Attaching a sealing material such as an O-ring to the joint portion may prevent the leakage, however providing the O-ring incurs frictional resistance at the joint portion, which inhibits smoothly rotating the distal tube 1A to which the high-frequency electrode is attached by manipulation of the flexible sheath 1 by hand, because the flexible sheath 1 is not only flexible but as slender as only approx. 2 mm in diameter over a length of 1 to 2 m.

SUMMARY OF THE INVENTION

Accordingly, the present invention is advantageous in that there is provided a high-frequency incision instrument for an endoscope that allows rotating a high-frequency electrode attached to a lateral surface close to a tip portion of a flexible sheath around its axial line by manipulation by hand, and also injecting irrigation water, whenever necessary, in a lateral direction from the lateral surface close to a tip portion of the flexible sheath.

The present invention provides a high-frequency incision instrument for an endoscope including an electrically insulative flexible sheath constituted of a distal tube disposed at a tip portion thereof and a proximal tube disposed on a proximal side such that one is loosely inserted into the other so as to rotate around an axial line thereof, a high-frequency electrode exposed along a lateral surface of the distal tube and connected to a conductive operating wire extending throughout inside the distal tube and the proximal tube, so that a high-frequency current is supplied to the high-frequency electrode through the operating wire, and so that rotating the operating wire at a proximal end portion of the proximal tube around an axial line causes the distal tube to rotate around the axial line with respect to the proximal tube, thus to change an orientation of the high-frequency electrode.

The high-frequency incision instrument for an endoscope is provided with a water inlet located at a proximal end portion of the proximal tube for supplying water into the proximal tube, a water injection outlet located on the lateral surface of the distal tube for injecting the water supplied into the proximal tube, and a seal ring that prevents the water from leaking through a joint portion between the distal tube and the proximal tube, attached to an outer surface of one of the distal tube and the proximal tube that is smaller in outer diameter. With such structure, pulling the operating wire toward a proximal side by manipulation by hand causes the seal ring to intrude into the joint portion between the distal tube and the proximal tube, to thereby prevent the water leakage, and pushing forward the operating wire by manipulation by hand releases the seal ring from the joint portion between the distal tube and the proximal tube, thereby allowing the distal tube to rotate following a rotating motion of the operating wire around the axial line, thus to change an orientation of the high-frequency electrode.

Also, the seal ring may be constituted of an elastic heat-shrunk tube and shrunk-fitted to an outer surface of one of the distal tube and the proximal tube that is smaller in outer diameter, and the high-frequency electrode may be constituted of a conductive wire exposed along an outer surface of the distal tube, through a pair of through holes aligned lengthwise on a lateral surface of the distal tube at an interval.

Further, at least one of the pair of through holes through which the wire electrode is disposed may also serve as the water injection outlet. Otherwise, the water injection outlet may be perforated on the lateral surface of the distal tube, in addition to the pair of through holes through which the wire electrode is disposed.

With the high-frequency incision instrument for an endoscope according to the present invention, pulling the operating wire toward a proximal side by manipulation by hand causes the seal ring to intrude into the joint portion between the distal tube and the proximal tube, to thereby prevent the water leakage, and pushing forward the operating wire by manipulation by hand releases the seal ring from the joint portion between the distal tube and the proximal tube, thereby allowing the distal tube to rotate following a rotating motion of the operating wire around the axial line, thus to change an orientation of the high-frequency electrode. The high-frequency incision instrument for an endoscope allows, therefore, smoothly rotating the high-frequency electrode provided on the lateral surface close to the tip portion of the flexible sheath around the axial line by manipulation at hand, and also injecting, whenever necessary, the irrigation water in a lateral direction from the lateral surface close to the tip portion of the flexible sheath to wash away the burnt residuum, thereby facilitating safely and precisely performing the subsequent high-frequency resection process.

BRIEF DESCRIPTION OF THE ACCOMPANYING DRAWINGS

DETAILED DESCRIPTION OF THE EMBODIMENTS

Hereunder, detailed description will be given on a high-frequency incision instrument for an endoscope according to the present invention. The high-frequency incision instrument includes an electrically insulative flexible sheath constituted of a distal tube disposed at a tip portion thereof and a proximal tube disposed on a proximal side such that one is loosely inserted into the other so as to rotate around an axial line thereof, a high-frequency electrode exposed along a lateral surface of the distal tube and connected to a conductive operating wire extending throughout inside the distal tube and the proximal tube, so that a high-frequency current is supplied to the high-frequency electrode through the operating wire, and so that rotating the operating wire at a proximal end portion of the proximal tube around an axial line causes the distal tube to rotate around the axial line with respect to the proximal tube thus to change an orientation of the high-frequency electrode, and also including a water inlet located at a proximal end portion of the proximal tube for supplying water into the proximal tube, a water injection outlet located on the lateral surface of the distal tube for injecting the water supplied into the proximal tube, and a seal ring that prevents the water from leaking through a joint portion between the distal tube and the proximal tube, attached to an outer surface of one of the distal tube and the proximal tube that is smaller in outer diameter, in which pulling the operating wire toward a proximal side by manipulation by hand causes the seal ring to intrude into the joint portion between the distal tube and the proximal tube, to thereby prevent the water leakage, and pushing forward the operating wire by manipulation by hand releases the seal ring from the joint portion between the distal tube and the proximal tube, thereby allowing the distal tube to rotate following a rotating motion of the operating wire around the axial line, thus to change an orientation of the high-frequency electrode.

Referring to the accompanying drawings, an exemplary embodiments of the present invention will be described hereunder.

Figure 2:
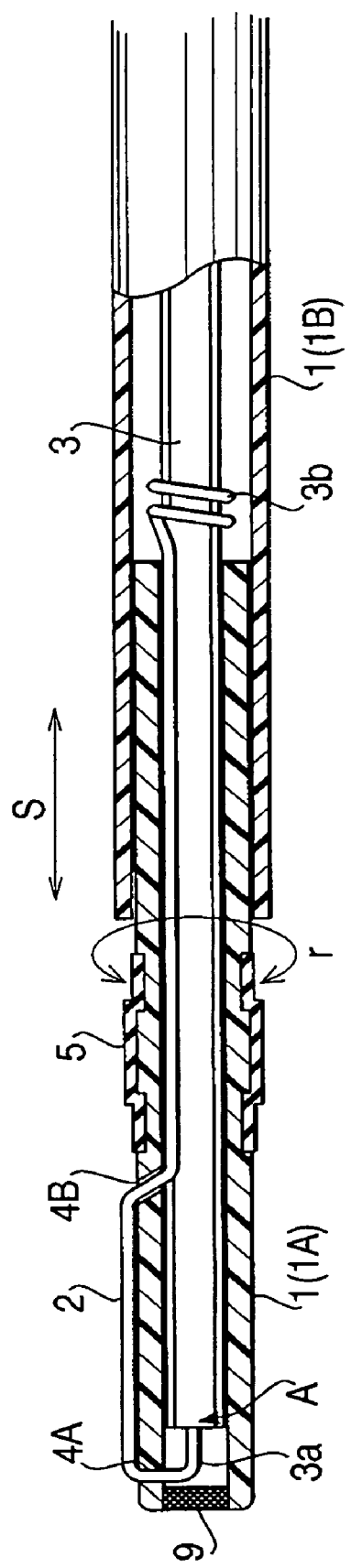
FIG. 2 is a lateral cross-sectional view showing an inverting action of a high-frequency electrode at a tip portion of the high-frequency incision instrument for an endoscope according to the first embodiment.

FIG. 2 depicts a tip portion of the high-frequency incision instrument for an endoscope according to a first embodiment.

In the high-frequency incision instrument, a high-frequency electrode 2 is exposed along a lateral surface close to the tip portion of a flexible sheath 1 constituted of an electrically insulative material such as 4-ethylene fluoride resin, and a conductive operating wire 3 inserted through the flexible sheath 1 is electrically and mechanically connected to the high-frequency electrode 2.

The flexible sheath 1 includes a distal tube 1A and a proximal tube 1B connected to each other, at a position close to the tip portion of the flexible sheath 1 and on an proximal side from the high-frequency electrode 2 (for instance, 1 to 10 cm from the tip portion of the flexible sheath 1). An opening at a forefront portion of the distal tube 1A is filled with a cap 9.

More specifically, the proximal tube 1B is approx. 1.5 to 3 mm in outer diameter and approx. 1 to 2 m in length for example, and the distal tube 1A has an outer diameter that can be loosely fitted into a tip portion of the proximal tube 1B is inserted thereinto in a depth of approx. 1 to 2 cm, so that the distal tube 1A is connected to the proximal tube 1B so as to relatively rotate around an axial line thereof and also axially slide, with respect to the proximal tube 1B.

The operating wire 3 is, in this embodiment, constituted of a straight core wire with a plurality (for instance, five or six) of element wires stranded around the core wire, and the core wire extends out of the tip portion of the element wires thus to constitute the high-frequency electrode 2, while the tip portion A of the element wires is mechanically crimp-fixed to a base portion of the extension 3a of the core wire. The element wires may be fixed by blazing or the like, instead.

On the lateral surface close to the tip portion of the distal tube 1A, a pair of through holes 4A, 4B is provided with an interval in a lengthwise direction. The extension 3a of the core wire of the operating wire 3 is led out from the through hole 4A on the distal side and bent backward, such that the bent portion is introduced into the distal tube 1A via the through hole 4B on the proximal side, and the extension 3a of the core wire exposed on the outer surface of the distal tube 1A between the pair of through holes 4A, 4B constitutes the wire-shaped high-frequency electrode 2.

The tip portion 3b of the extension of the core wire introduced backward into the distal tube 1A via the through hole 4B on the proximal side extends into the proximal tube 1B past the distal tube 1A, and is wound around the operating wire 3 inside the proximal tube 1B, at a position close the a tip portion thereof. With such arrangement, the tip portion of the operating wire 3 is substantially fixed to the distal tube 1A.

Accordingly, when the operating wire 3 is rotated around its axial line by remote operation by hand, the distal tube 1A is rotated as indicated by the arrow r around the axial line with respect to the proximal tube 1B so as to change the orientation of the high-frequency electrode 2, and when the operating wire 3 is moved back and forth in an axial direction, the distal tube 1A is moved as indicated by the arrow S in the axial direction with respect to the proximal tube 1B.

At a position on the outer surface of the distal tube 1A slightly backward from the through hole 4B on the proximal side, a seal ring 5 made of a heat-shrunk tube of an elastic material is closely fixed by-a heat-shrinking process. The distal tube 1A is formed with a recess provided at positions on the surface thereof corresponding to the respective end portions of the seal ring 5.

Figure 1:
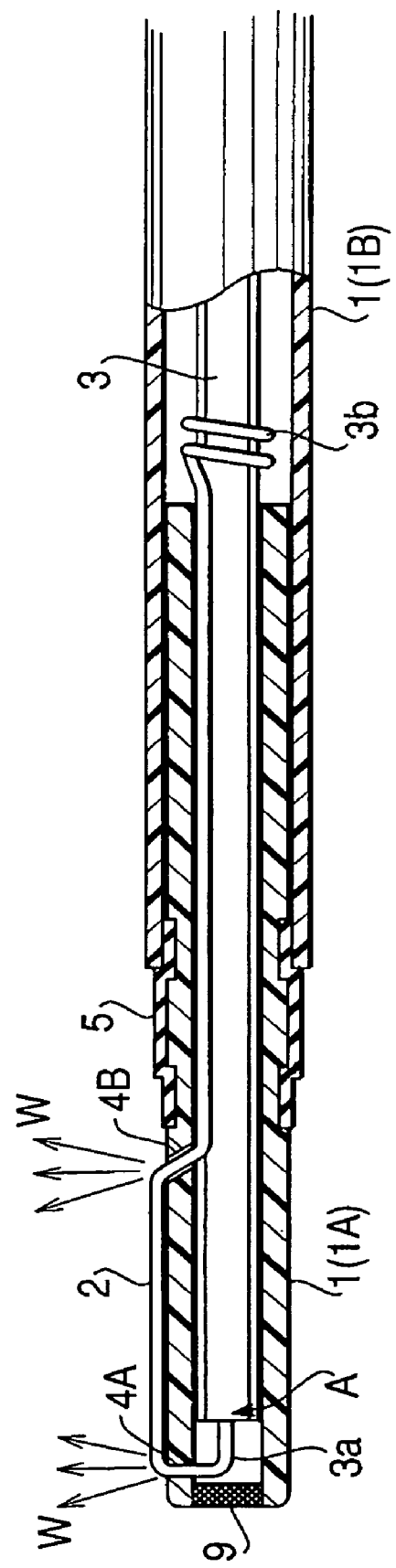
FIG. 1 is a lateral cross-sectional view showing a water injection mode in a high-frequency incision instrument for an endoscope according to a first embodiment of the present invention.

Thus, the seal ring 5 is securely fixed to the distal tube 1A so as not to shift in the axial direction with respect thereto and, as shown in FIG. 1, when the distal tube 1A is pulled backward by the operating wire 3, the backward portion of the seal ring 5 is slightly elastically deformed so as to be press-inserted into the proximal tube 1B to achieve a close contact therewith, so that the joint portion between the distal tube 1A and the proximal tube 1B is sealed and water leakage is thereby prevented.

The region close to the central portion of the seal ring 5 is butted to the forward facet of the proximal tube 1B when the distal tube 1A is pulled backward by the operating wire 3, thereby serving as a stopper that keeps the distal tube 1A from intruding into the proximal tube 1B.

Under such state, when the operating wire 3 is pushed forward by manipulation by hand, the distal tube 1A is moved forward with respect to the proximal tube 1B thus to be situated as shown in FIG. 2 again, and in this process the operating wire 3 serves as a stopper that keeps the distal tube 1A from coming off from the proximal tube 1B.

Figure 3:
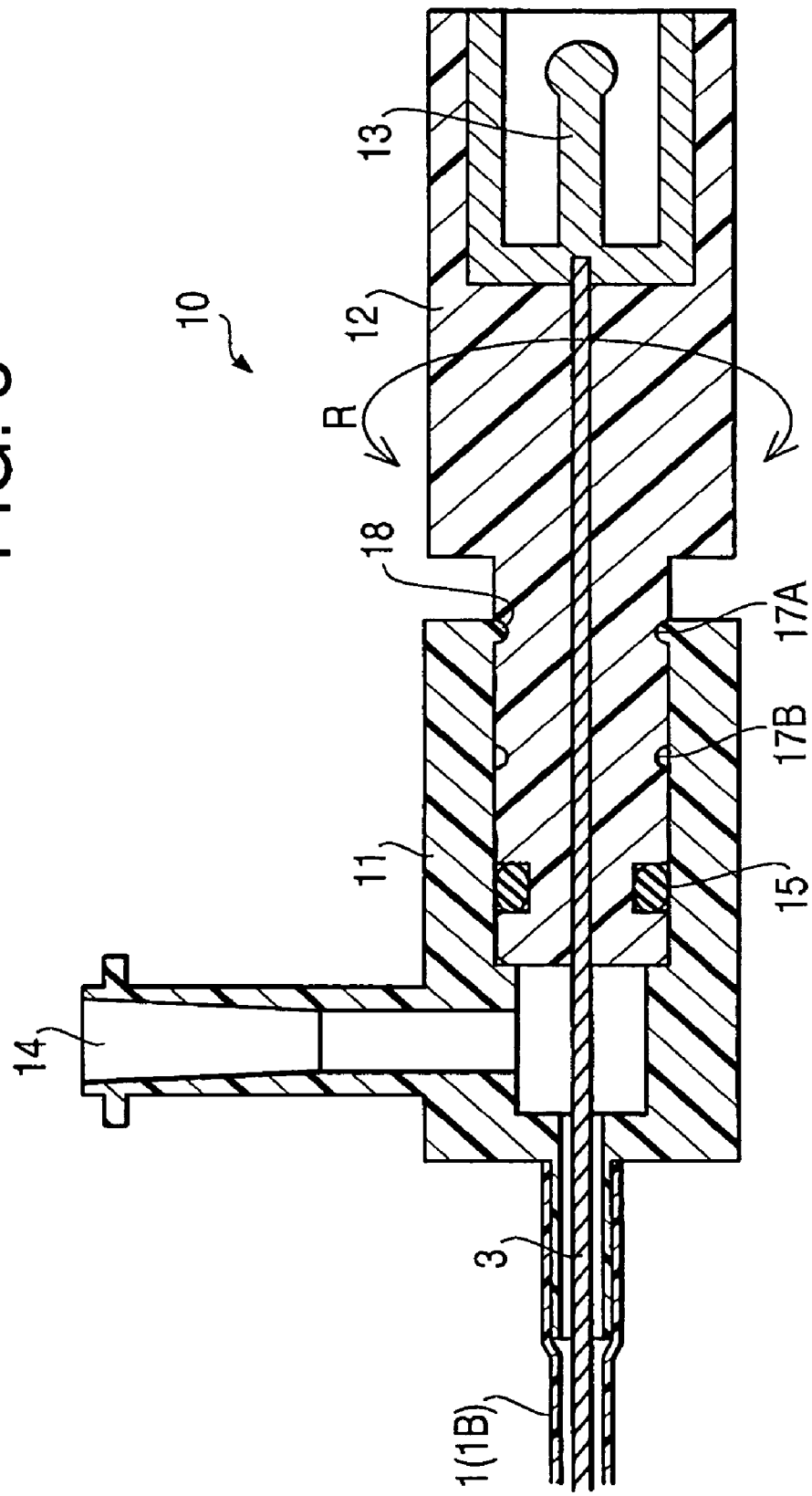
FIG. 3 is a lateral cross-sectional view showing an inverting action of a high-frequency electrode by an operating unit of the high-frequency incision instrument for an endoscope according to the first embodiment.

FIG. 3 depicts an operating unit 10 provided at a proximal end portion of the flexible sheath 1, in which a proximal end portion of the proximal tube 1B is fixedly connected to a tip portion of a cylindrical operating unit main body 11, and a proximal end portion of the operating wire 3 is insert-fixed into a manipulator 12, having a forward half portion thereof insert-fitted into the operating unit main body 11.

The manipulator 12 includes a connection terminal 13 to which a high-frequency power cable (not shown) is to be connected, so as to supply a high-frequency current to the high-frequency electrode 2 through the operating wire 3, when necessary.

Figure 4:
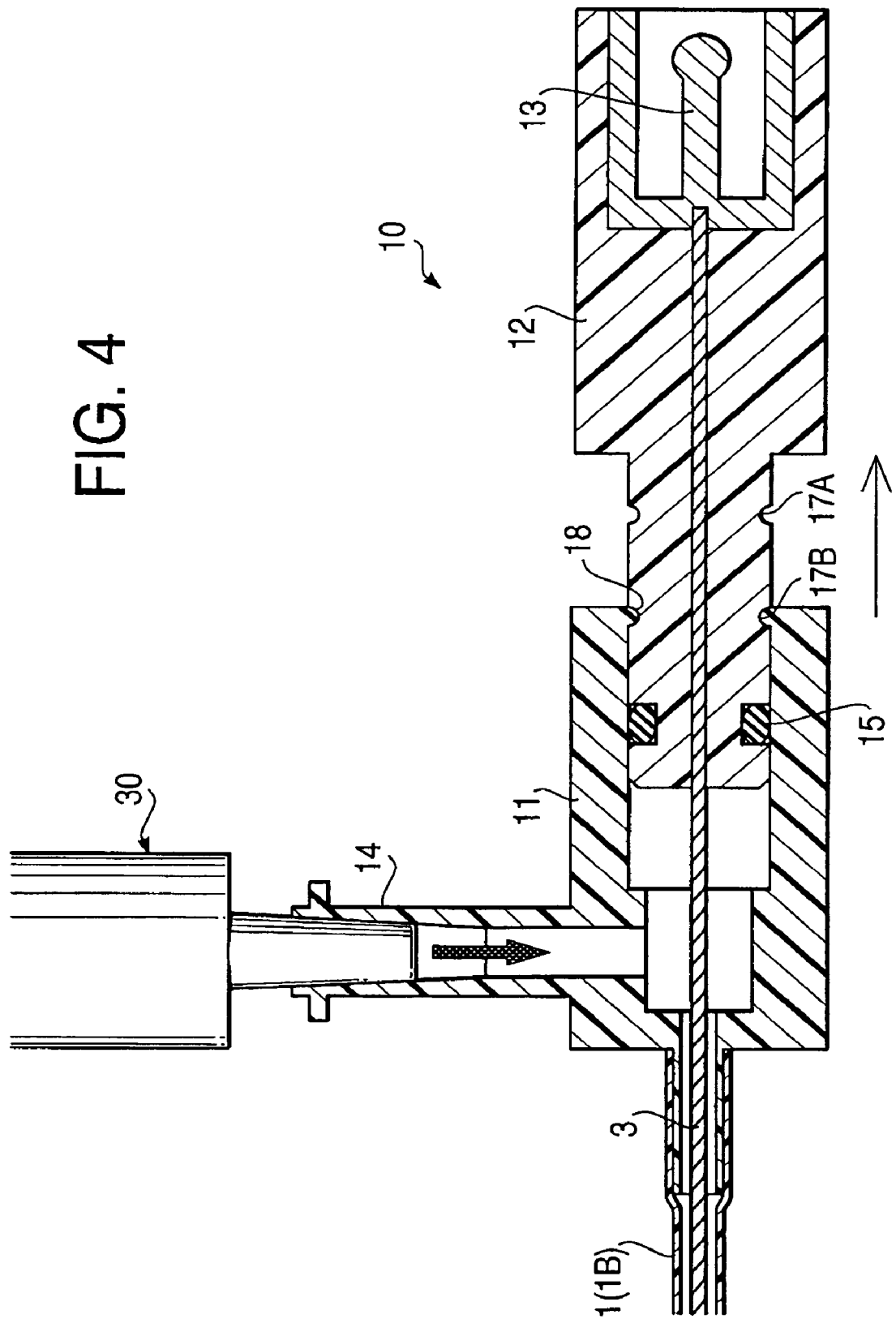
FIG. 4 is a lateral cross-sectional view showing an action of the operating unit for water injection, in a high-frequency incision instrument for an endoscope according to the first embodiment.

On a lateral face of the operating unit main body 11, a water inlet 14 is projected so as to communicate with the inside of the proximal tube 1B, so that upon connecting a water feeder 30 to the water inlet 14 as shown in FIG. 4, irrigation water or the like can be supplied into the proximal tube 1B when necessary. Reference numeral 15 designates an O-ring for sealing, which serves to prevent the irrigation water injected into the operating unit main body 11 through the water inlet 14 from leaking through the fitting portion with the manipulator 12.

The manipulator 12 can be moved in an axial direction with respect to the operating unit main body 11, so that the operating wire 3 is axially moved back and forth inside the proximal tube 1B. To elastically retain the positional relationship between the operating unit main body 11 and the manipulator 12 defined by the back-and-forth movement, a click mechanism is provided.

The click mechanism according to this embodiment includes two circumferential grooves 17A, 17B formed on an outer circumferential surface of the manipulator 12 with an interval in an axial direction, and a protrusion 18 formed so as to slightly protrude from an inner circumferential surface of the operating unit main body 11 to be engaged with the circumferential grooves 17A, 17B.

Under such structure, while the protrusion 18 is engaged with either of the circumferential grooves 17A, 17B as shown in FIGS. 3 and 4, the manipulator 12 is fixed to the operating unit main body 11, and when a force of an appropriate magnitude is applied to push forward or pull backward the manipulator 12 with respect to the operating unit main body 11, the manipulator 12 is released from the click engagement, thus to be freely movable with respect to the operating unit main body 11.

In the high-frequency incision instrument for an endoscope thus configured according to this embodiment, when the manipulator 12 is pushed forward into the operating unit main body 11 as shown in FIG. 3, on the distal side the seal ring 5 is released from the tip portion of the proximal tube 1B as shown in FIG. 2.

Then when the operator rotates the manipulator 12 around the axial line as indicated by the arrow R in FIG. 3 while holding the operating unit main body 11, the operating wire 3 is caused to rotate around the axial line inside the proximal tube 1B, which causes the distal tube 1A to rotate around the axial line with respect to the proximal tube 1B as indicated by the arrow r in FIG. 2, thereby causing the high-frequency electrode 2 to rotate around the axial line of the distal tube 1A.

Under such state, although the water feeder 30 is connected to the water inlet 14 and the irrigation water or the like is injected into the proximal tube 1B, the irrigation water leaks through the joint portion with the distal tube 1A. Accordingly, when supplying the irrigation water, the manipulator 12 is pulled backward with respect to the operating unit main body 11 as shown in FIG. 4, so that on the distal side the seal ring 5 is press-inserted into the tip portion of the proximal tube 1B as shown in FIG. 1, thus to seal the tip portion of the proximal tube 1B.

When the irrigation water is supplied from the water feeder 30 under the above state, the irrigation water is injected in a lateral direction through the clearance between the high-frequency electrode 2 and the respective through holes 4A, 4B, as shown in FIG. 1. Thus, in this embodiment the two through holes 4A, 4B also serve as the water injection outlet. Meanwhile, it suffices that the irrigation water is injected through at least either of the through holes 4A, 4B.

Figure 5:
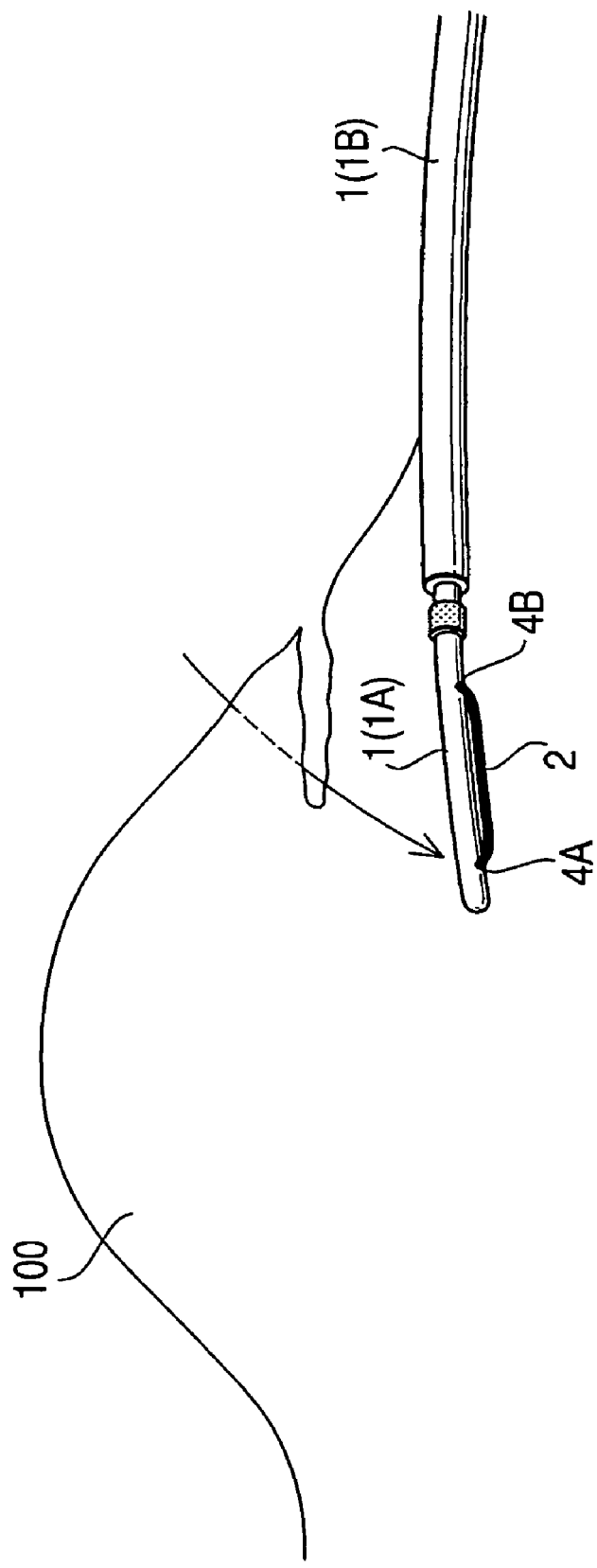
FIG. 5 is a schematic drawing showing a mucosal incision process by the high-frequency incision instrument for an endoscope according to the first embodiment.
Figure 6:
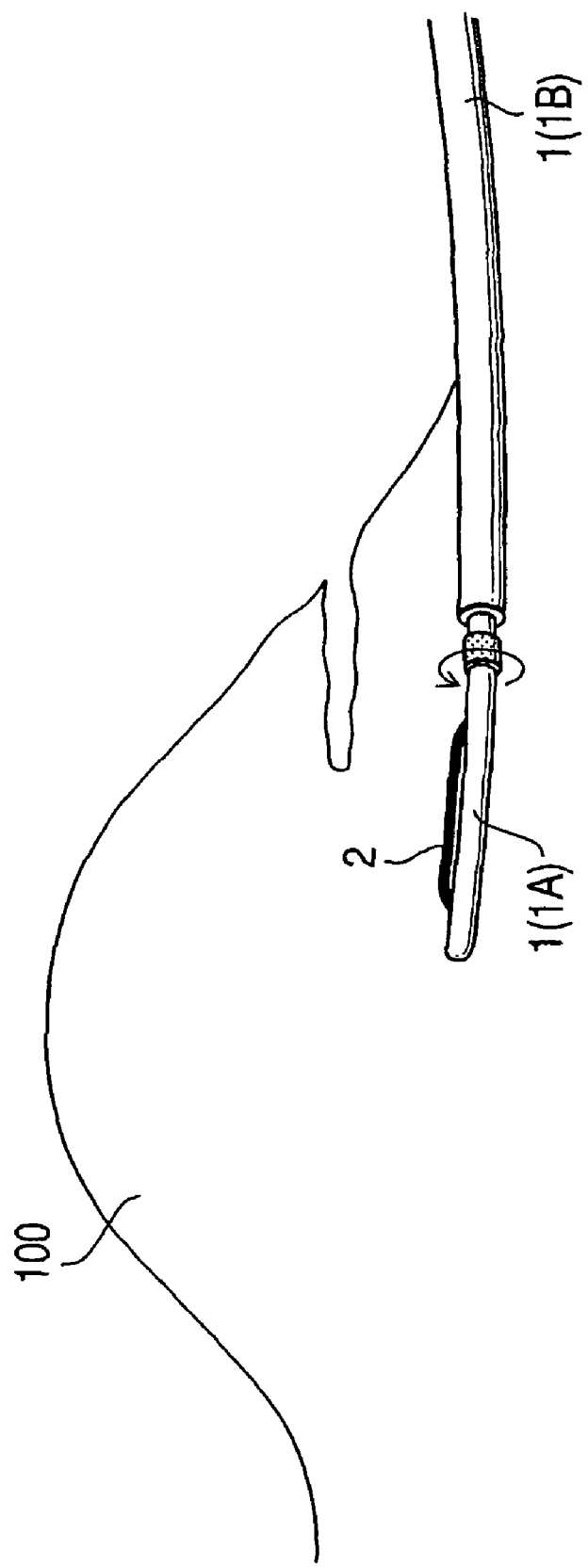
FIG. 6 is a schematic drawing showing another step of the mucosal incision process by the high-frequency incision instrument for an endoscope according to the first embodiment.
Figure 7:
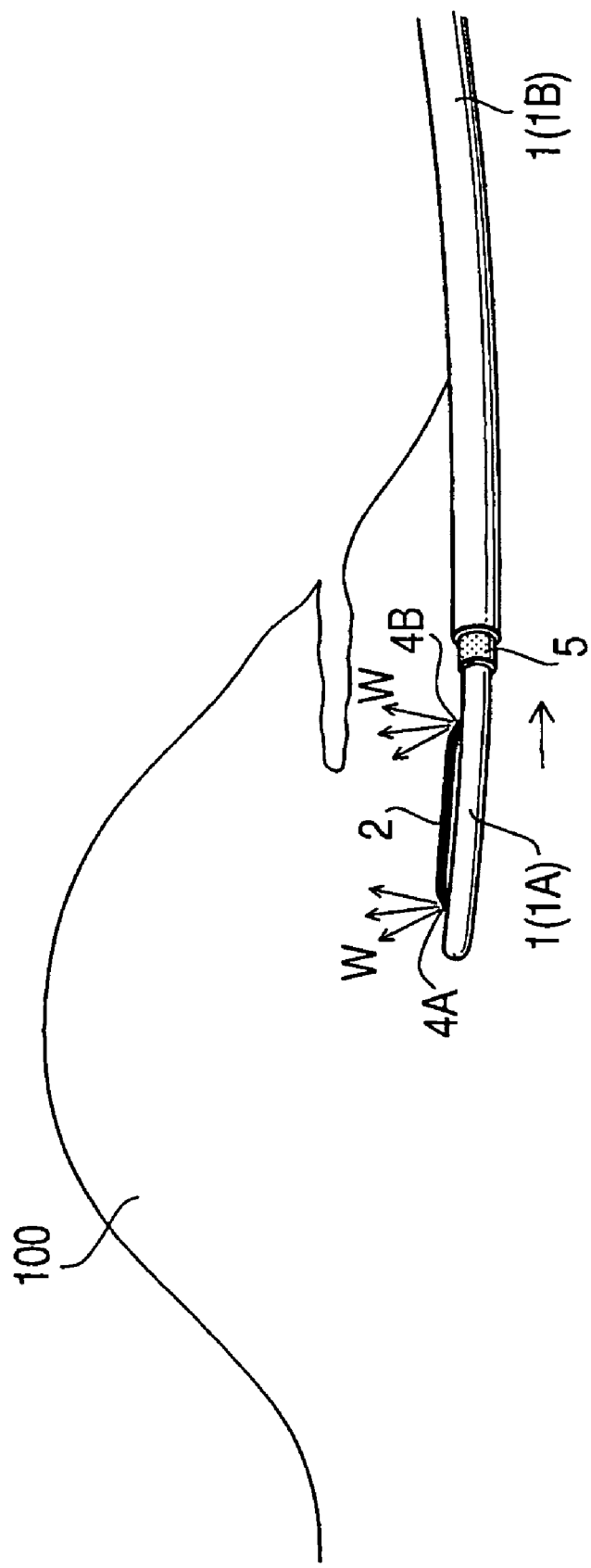
FIG. 7 is a schematic drawing showing still another step of the mucosal incision process by the high-frequency incision instrument for an endoscope according to the first embodiment.

FIGS. 5 to 7 illustrate a process of incising the bulge 100 on the mucous membrane in a horizontal direction with the high-frequency incision instrument for an endoscope according to the foregoing embodiment. After inserting the flexible sheath 1 through the instrument insertion channel (not shown) of the endoscope, the manipulator 12 is rotated so as to rotate the distal tube 1A such that the high-frequency electrode 2 is suitably oriented for the incision, and the flexible sheath 1 is caused to swing as shown in FIG. 5, with a high-frequency current being supplied to the high-frequency electrode 2, thus to perform the first horizontal incision of the bulge 100.

Then as shown in FIG. 6, the manipulator 12 is rotated holding the proximal tube 1B immobile at the current position, so as to rotate the distal tube 1A such that the high-frequency electrode 2 is inverted by 180 degrees. Such action sets the high-frequency incision instrument ready for consecutively performing the second horizontal incision of the bulge 100.

Here, placing a mark on the distal tube 1A at a position opposite to the high-frequency electrode 2 enables correctly identifying the orientation of the high-frequency electrode 2 in view of the position of the mark through the endoscopic observation, even when the high-frequency electrode 2 is not visibly oriented in the endoscope.

When it is necessary to wash away the burnt residuum that has splashed during the first incision, the distal tube 1A is pulled backward as shown in FIG. 7, so as to press-insert the seal ring 5 into the tip portion of the proximal tube 1B, and the irrigation water is injected in a lateral direction from the distal tube 1A as indicated by the arrow W, after which the second horizontal incision is performed.

Figure 8:
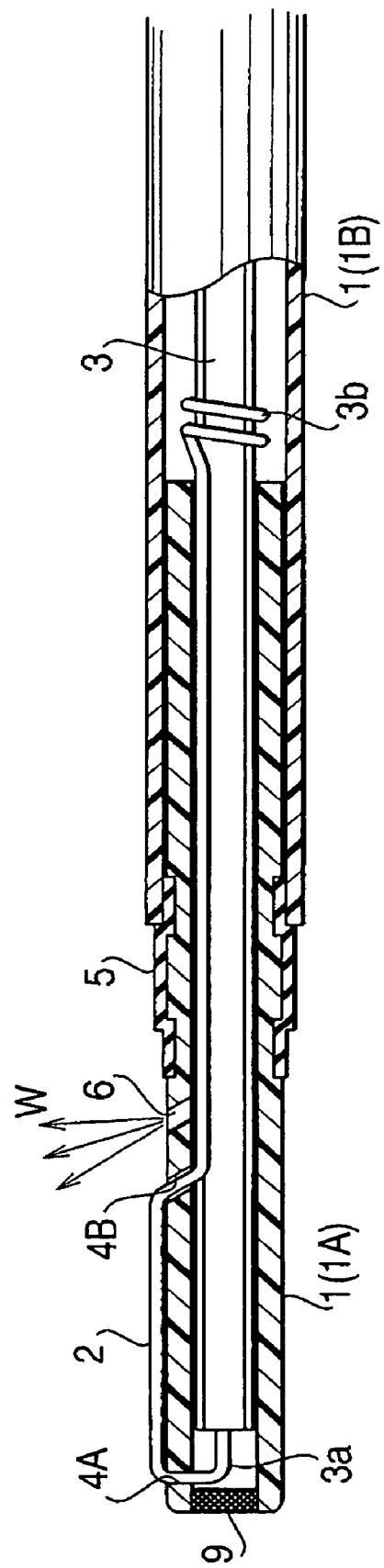
FIG. 8 is a lateral cross-sectional view showing a water injection mode in a high-frequency incision instrument for an endoscope according to a second embodiment of the present invention.
Figure 9:
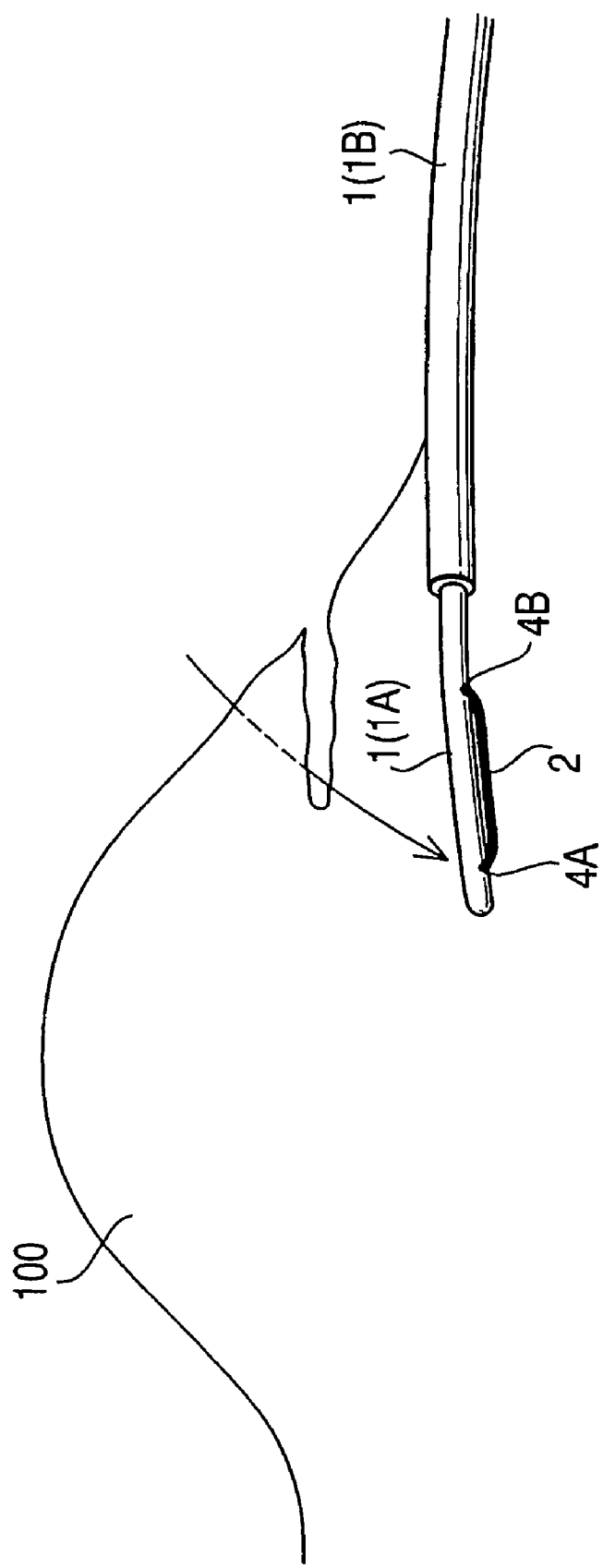
FIG. 9 is a schematic drawing showing a mucosal incision process by a conventional high-frequency incision instrument for an endoscope.
Figure 10:
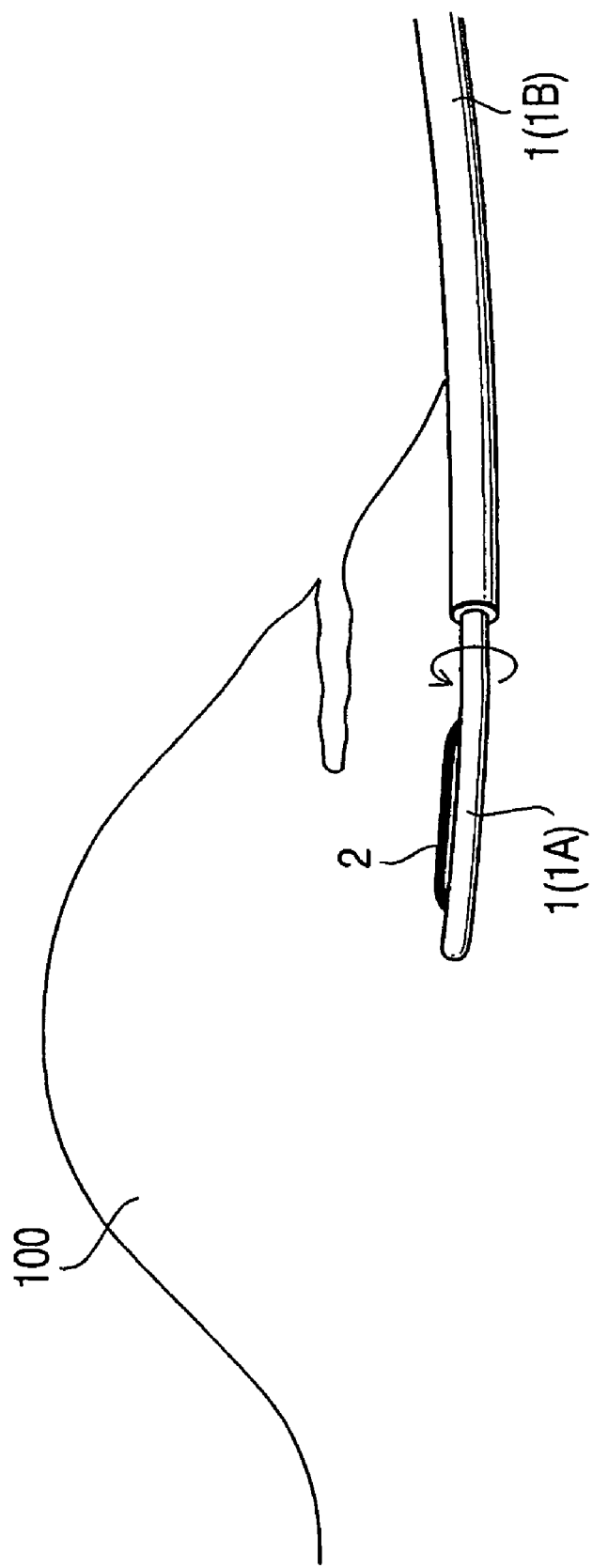
FIG. 10 is a schematic drawing showing another step of the mucosal incision process by the conventional high-frequency incision instrument for an endoscope.
Figure 11:
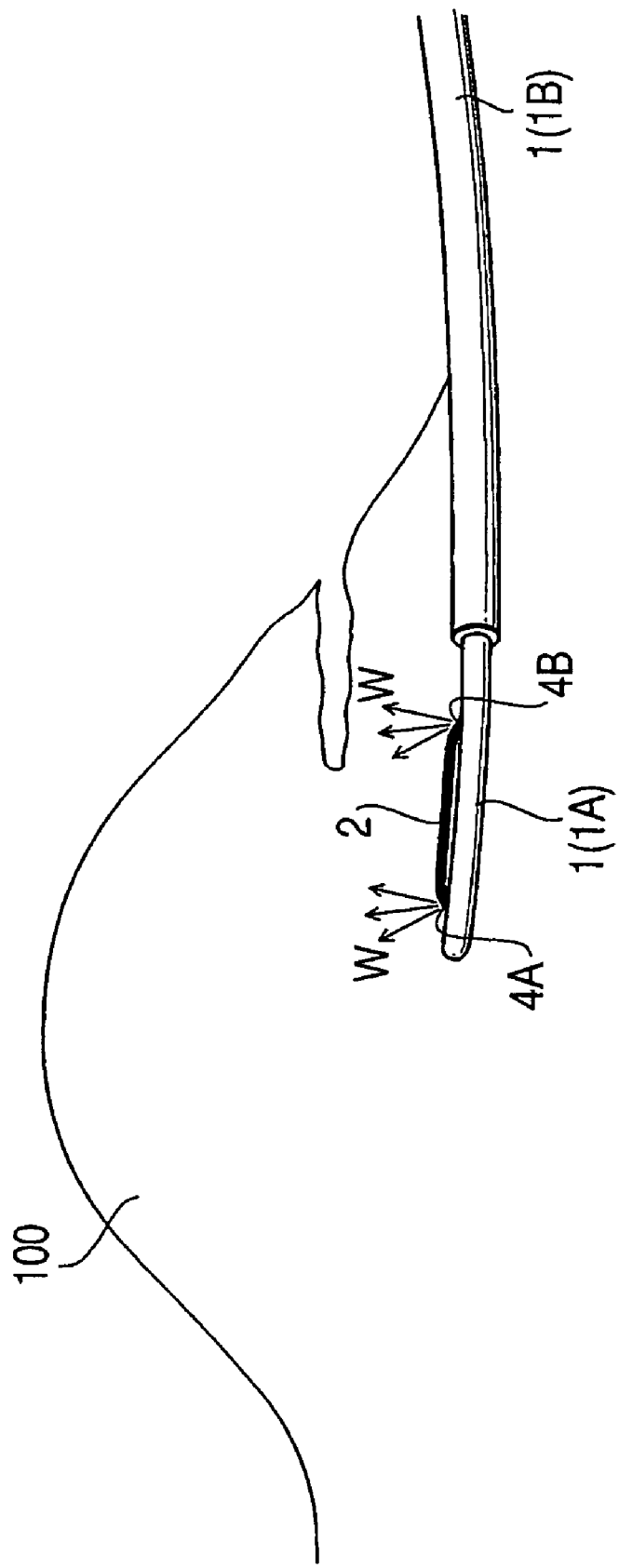
FIG. 11 is a schematic drawing showing still another step of the mucosal incision process by the conventional high-frequency incision instrument for an endoscope.
Figure 12:
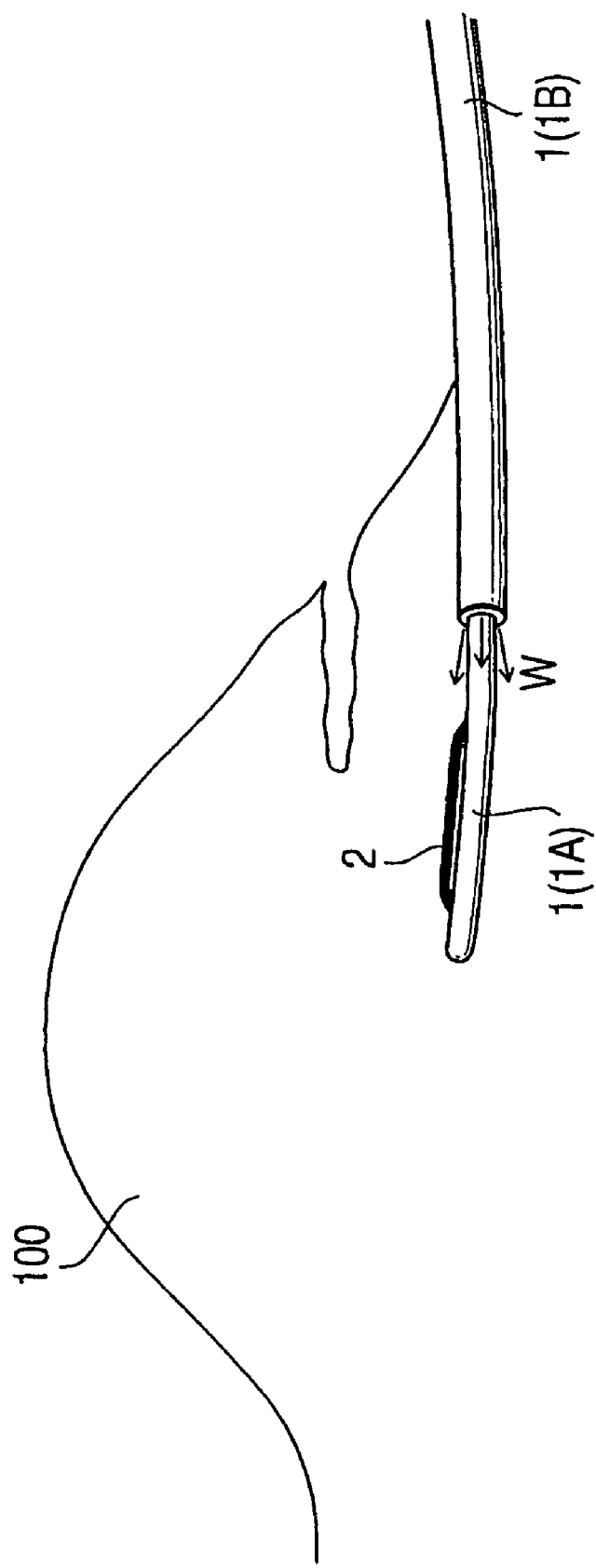
FIG. 12 is a schematic drawing showing still another step of the mucosal incision process by the conventional high-frequency incision instrument for an endoscope.

It should be noted that the present invention is not limited to the foregoing embodiment, and that, as in FIG. 8, which shows a second embodiment, a water injection outlet 6 may be independently provided on the lateral surface of the distal tube 1A in addition to the pair of through holes 4A, 4B, so that the irrigation water is injected exclusively from the water injection outlet 6, in a lateral direction as indicated by the arrow W Also, while the distal tube 1A is inserted into the proximal tube 1B for connection according to the foregoing embodiment, on the contrary the proximal tube 1B may be formed in a smaller diameter than the distal tube 1A, so as to insert the proximal tube 1B into the distal tube 1A for connection. In this case, the seal ring 5 is attached to the proximal tube 1B.

Further, various ring-shaped materials may be employed as the seal ring 5, without limitation to the heat-shrunk tube.

What is claimed is:

1. A high-frequency incision instrument for an endoscope including an electrically insulative flexible sheath constituted of a distal tube disposed at a tip portion thereof and a proximal tube disposed on a proximal side such that one is loosely inserted into the other so as to rotate around an axial line thereof, a high-frequency electrode exposed along a lateral surface of the distal tube and connected to a conductive operating wire extending throughout inside the distal tube and the proximal tube, so that a high-frequency current is supplied to the high-frequency electrode through the operating wire, and so that rotating the operating wire at a proximal end portion of the proximal tube around an axial line causes the distal tube to rotate around the axial line with respect to the proximal tube thus to change an orientation of the high-frequency electrode, comprising:

a water inlet located at a proximal end portion of the proximal tube for supplying water into the proximal tube; a water injection outlet located on the lateral surface of the distal tube for injecting the water supplied into the proximal tube out of the distal tube; and a seal ring that prevents the water from leaking through a joint portion between the distal tube and the proximal tube, attached to an outer surface of one of the distal tube and the proximal tube that is smaller in outer diameter, wherein pulling the operating wire toward a proximal side by manipulation by hand causes the seal ring to intrude into the joint portion between the distal tube and the proximal tube, to thereby prevent the water leakage, and pushing forward the operating wire by manipulation by hand releases the seal ring from the joint portion between the distal tube and the proximal tube, thereby allowing the distal tube to rotate following a rotating motion of the operating wire around the axial line, thus to change an orientation of the high-frequency electrode.

2. The high-frequency incision instrument for an endoscope according to claim 1, wherein the high-frequency electrode includes a conductive wire exposed along an outer surface of the distal tube, through a pair of through holes aligned lengthwise on a lateral surface of the distal tube at an interval.

3. The high-frequency incision instrument for an endoscope according to claim 2, wherein at least one of the pair of through holes through which the wire electrode is disposed also serves as the water injection outlet.

4. The high-frequency incision instrument for an endoscope according to claim 2, wherein the water injection outlet is independently provided on the lateral surface of the distal tube, in addition to the pair of through holes through which the wire electrode is disposed.

* * * * *